United States Patent
Garcia Molina et al.

(10) Patent No.: US 10,994,092 B2
(45) Date of Patent: May 4, 2021

(54) SYSTEM AND METHOD FOR ADJUSTING THE INTENSITY OF SENSORY STIMULATION DURING SLEEP BASED ON SLEEP DEPTH

(71) Applicant: KONINKLIJKE PHILIPS N.V., Eindhoven (NL)

(72) Inventors: Gary Nelson Garcia Molina, Madison, WI (US); Anandi Mahadevan, Murrysville, PA (US); Surya Subrahmanya Sreeram Vissapragada Venkata Satya, Monroeville, PA (US); John Gerthoffer, Monroeville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 393 days.

(21) Appl. No.: 16/062,721

(22) PCT Filed: Dec. 8, 2016

(86) PCT No.: PCT/IB2016/057421
§ 371 (c)(1),
(2) Date: Jun. 15, 2018

(87) PCT Pub. No.: WO2017/109621
PCT Pub. Date: Jun. 29, 2017

(65) Prior Publication Data
US 2018/0361110 A1 Dec. 20, 2018

Related U.S. Application Data

(60) Provisional application No. 62/270,947, filed on Dec. 22, 2015.

(51) Int. Cl.
*A61M 21/02* (2006.01)
*A61B 5/0484* (2006.01)
(Continued)

(52) U.S. Cl.
CPC .......... *A61M 21/02* (2013.01); *A61B 5/0478* (2013.01); *A61B 5/04845* (2013.01);
(Continued)

(58) Field of Classification Search
CPC ... A61M 21/02; A61B 5/4812; A61N 1/36078
See application file for complete search history.

(56) References Cited

U.S. PATENT DOCUMENTS

| | | |
|---|---|---|
| 2008/0195166 A1 | 8/2008 | Sun et al. |
| 2014/0057232 A1 | 2/2014 | Anderson |

(Continued)

FOREIGN PATENT DOCUMENTS

| | | |
|---|---|---|
| WO | 2009112944 A2 | 9/2009 |
| WO | 2014118654 A1 | 8/2014 |
| WO | 2014170781 A1 | 10/2014 |

OTHER PUBLICATIONS

M. Bellesi, B. Riedner, G. Garcia-Molina, C. Cirelli, and G. Tononi, "Enhancement of sleep slow waves: underlying mechanisms and practical consequences," Front. Syst. Neurosci., vol. 8, No. October, pp. 1-17, Oct. 2014.

(Continued)

*Primary Examiner* — Kaylee R Wilson

(57) ABSTRACT

The present disclosure pertains to a system configured to adjust an intensity of sensory stimulation delivered to a subject during a sleep session based on sleep depth in the subject during the sleep session. The restorative value of sleep may be increased by enhancing sleep slow-waves using sensory stimulation. The stimulation may be applied at an appropriate timing and/or intensity to enhance sleep slow-waves to enhance slow-waves without disturbing sleep.

21 Claims, 6 Drawing Sheets

(51) Int. Cl.
*A61B 5/00* (2006.01)
*A61N 1/36* (2006.01)
*A61B 5/0478* (2006.01)
*A61M 21/00* (2006.01)
*A61B 5/0482* (2006.01)

(52) U.S. Cl.
CPC .......... *A61B 5/4812* (2013.01); *A61B 5/4836* (2013.01); *A61N 1/36025* (2013.01); *A61B 5/0482* (2013.01); *A61B 5/6803* (2013.01); *A61M 2021/0016* (2013.01); *A61M 2021/0022* (2013.01); *A61M 2021/0027* (2013.01); *A61M 2021/0044* (2013.01); *A61M 2021/0072* (2013.01); *A61M 2205/505* (2013.01); *A61M 2205/52* (2013.01); *A61M 2230/10* (2013.01); *A61N 1/36034* (2017.08); *A61N 1/36078* (2013.01)

(56) References Cited

U.S. PATENT DOCUMENTS

2015/0374951 A1   12/2015   Garcia Molina et al.
2016/0302718 A1   10/2016   Laura Lapoint et al.

OTHER PUBLICATIONS

B. A. Riedner, B. K. Hulse, F. Ferrarelli, S. Sarasso, and G. Tononi, "Enhancing sleep slow waves with natural stimuli," Medicamundi, vol. 45, No. 2, pp. 82-88, 2010.

G. Garcia-Molina, M. Bellesi, S. Pastoor, S. Pfundtner, B. A. Riedner, and G. Tononi, "Online Single EEG Channel Based Automatic Sleep Staging," in Engineering Psychology and Cognitive Ergonomics. Applications and Services, D. Harris, Ed. Springer Berlin Heidelberg, 2013, pp. 333-342.

SYSTEM AND METHOD FOR ADJUSTING THE INTENSITY OF SENSORY STIMULATION DURING SLEEP BASED ON SLEEP DEPTH

CROSS-REFERENCE TO PRIOR APPLICATIONS

This application is the U.S. National Phase application under 35 U.S.C. § 371 of International Application Serial No. PCT/IB2016/057421, filed on 8 Dec. 2016, which claims the benefit of U.S. Application Ser. No. 62/270,947, filed on 22 Dec. 2015. These applications are hereby incorporated by reference herein.

BACKGROUND

1. Field

The present disclosure pertains to a system configured to adjust an intensity of sensory stimulation delivered to a subject during a sleep session based on sleep depth in the subject during the sleep session.

2. Description of the Related Art

Systems for monitoring sleep are known. Sensory stimulation during sleep is known. Sensory stimulation during sleep is often applied continuously and/or at intervals and intensities that do not correspond to sleeping patterns of a subject. The present disclosure overcomes deficiencies in prior art systems.

SUMMARY

Accordingly, one or more aspects of the present disclosure relate to a system configured to adjust an intensity of sensory stimulation delivered to a subject during a sleep session. The system comprises one or more sensory stimulators, one or more sensors, one or more hardware processors, and/or other components. The one or more sensory stimulators are configured to provide sensory stimulation to the subject. The one or more sensors are configured to generate output signals conveying information related to brain activity in the subject during the sleep session. The one or more hardware processors operatively communicate with the one or more sensory stimulators and the one or more sensors. The one or more hardware processors are configured by machine-readable instructions to: determine brain activity parameters in the subject during the sleep session based on the output signals, the brain activity parameters including one or more of a ratio of power in a slow frequency band of an electroencephalogram (EEG) signal to power in a high frequency band, a density of slow waves in the subject, or a peak to peak amplitude of the slow waves in the subject; determine sleep depth in the subject during the sleep session based on one or more of the ratio, the density of slow waves, or the peak to peak slow wave amplitude; and control the one or more sensory stimulators to adjust the intensity of sensory stimulation provided to the subject during the sleep session based on the determined sleep depth.

Yet another aspect of the present disclosure relates to a method for adjusting an intensity of sensory stimulation delivered to a subject during a sleep session with an adjustment system. The system comprises one or more sensory stimulators, one or more sensors, one or more hardware processors, and/or other components. The method comprises: generating, with the one or more sensors, output signals conveying information related to brain activity in the subject during the sleep session; determining, with the one or more hardware processors, brain activity parameters in the subject during the sleep session based on the output signals, the brain activity parameters including one or more of a ratio of power in a slow frequency band of an electroencephalogram (EEG) signal to power in a high frequency band, a density of slow waves in the subject, or a peak to peak amplitude of the slow waves in the subject; determining sleep depth in the subject during the sleep session based on one or more of the ratio, the density of slow waves, or the peak to peak slow wave amplitude; and controlling the one or more sensory stimulators to adjust the intensity of sensory stimulation provided to the subject during the sleep session based on the determined sleep depth.

Still another aspect of present disclosure relates to a system for adjusting an intensity of sensory stimulation delivered to a subject during a sleep session. The system comprises: means for providing sensory stimulation to the subject; means for generating output signals conveying information related to brain activity in the subject during the sleep session; means for determining brain activity parameters in the subject during the sleep session based on the output signals, the brain activity parameters including one or more of a ratio of power in a slow frequency band of an electroencephalogram (EEG) signal to power in a high frequency band, a density of slow waves in the subject, or a peak to peak amplitude of the slow waves in the subject; means for determining sleep depth in the subject during the sleep session based on one or more of the ratio, the density of slow waves, or the peak to peak slow wave amplitude; and means for controlling the means for providing sensory stimulation to adjust the intensity of sensory stimulation provided to the subject during the sleep session based on the determined sleep depth.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
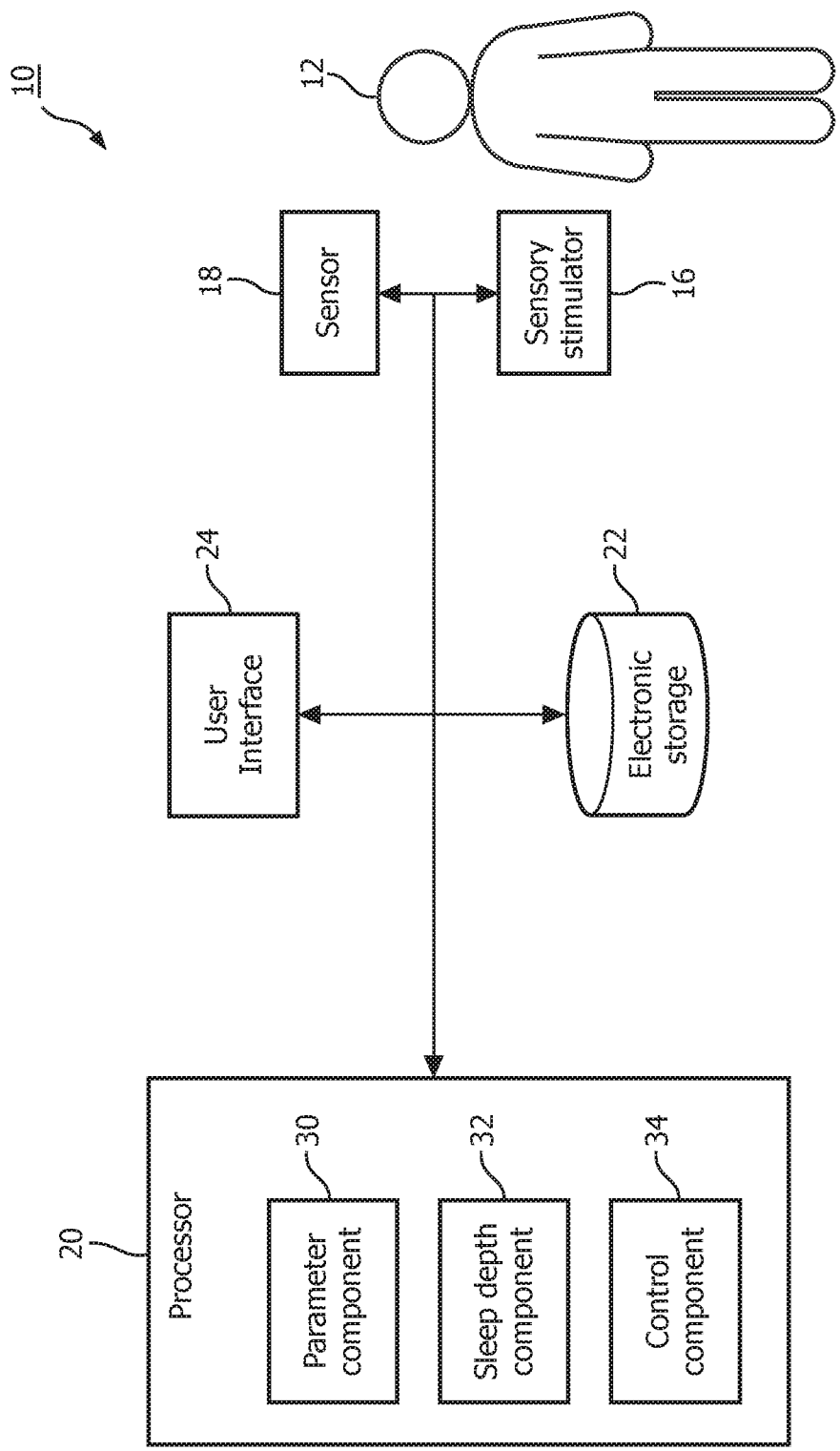
FIG. 1 illustrates a system configured to adjust an intensity of sensory stimulation delivered to a subject during a sleep session based on sleep depth in the subject during the sleep session.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to adjust an intensity of sensory stimulation delivered to a subject 12 during a sleep session based on sleep depth in subject 12 during the sleep session. The restorative value of sleep may be increased by enhancing sleep slow-waves using sensory stimulation. The stimulation may be applied at an appropriate timing and/or intensity to enhance slow-waves without disturbing sleep. Stimulation intensity adjustment mechanisms currently implemented in prior art systems are known to include controls which sometimes apply the loudest stimulation during lighter sleep and apply low volume stimulation while sleep is deep enough to allow for louder stimulation.

Figure 2:
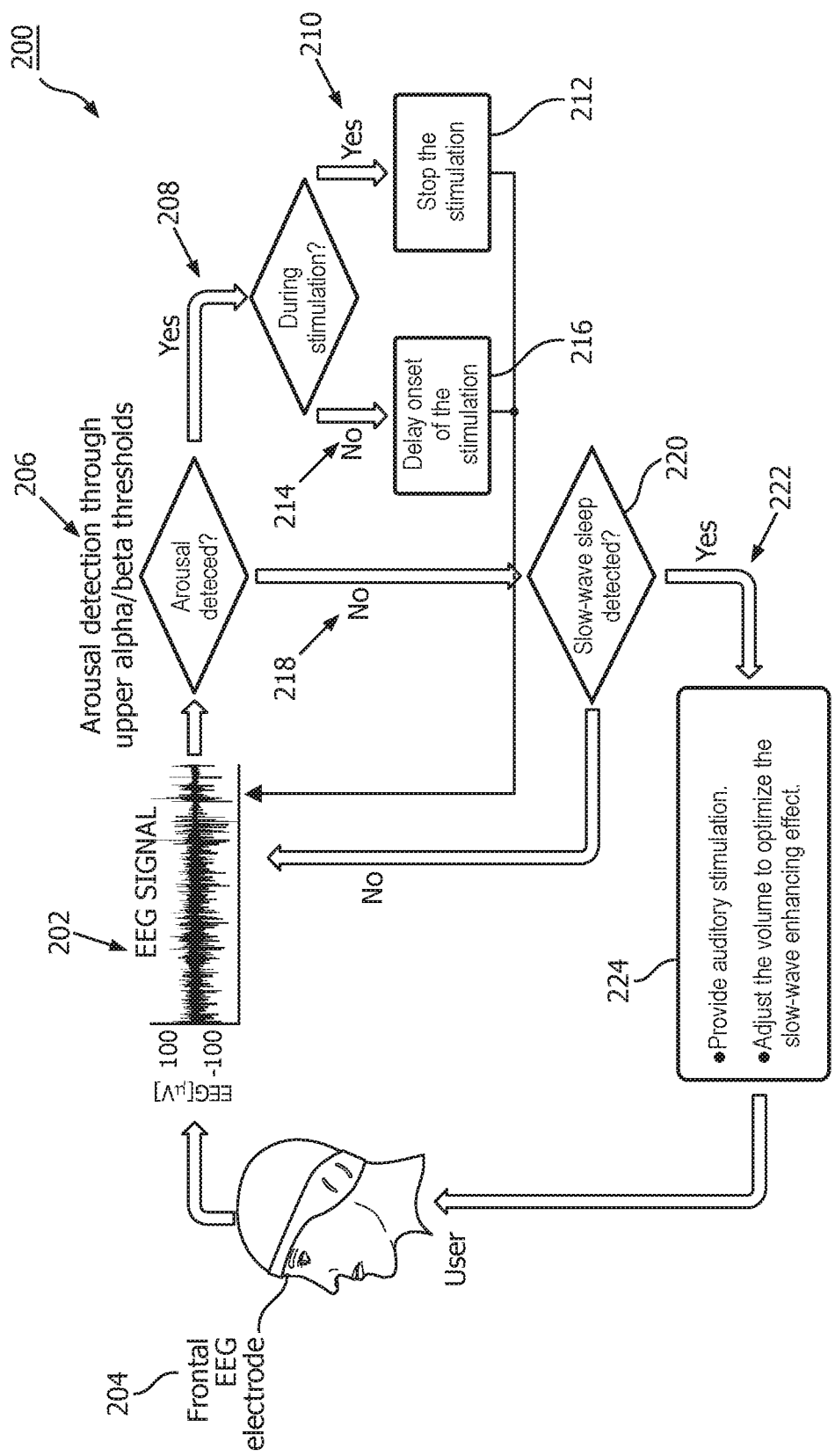
FIG. 2 illustrates operations performed by an EEG-based system configured to automatically detect periods of NREM sleep during which stimulation can be delivered with a low risk of causing arousals.

FIG. 2 summarizes operations 200 performed by an electroencephalogram (EEG) 202 based system configured to automatically detect periods of NREM sleep (described below) during which stimulation can be delivered with a low risk of causing arousals. The system uses a signal from a frontal EEG electrode 204 referenced to the right mastoid. The system first determines 206 the presence (or the likelihood) of sleep micro-arousals using upper thresholds on EEG power in the alpha (about 8-12 Hz) and beta (about 15-30 Hz) bands. If either of the power in the alpha or in the beta band exceeds its respective predefined threshold for a sufficiently long period of time, then the system determines 208 that a micro-arousal has occurred. If a micro-arousal occurs while the stimulation is being applied 210, then the stimulation stops 212 and resumes when the system detects a stable deep sleep for a predefined period of time. If a micro-arousal is detected in a period without stimulation 214, then the onset of the next stimulation is delayed 216. In the absence of micro-arousals 218, the system detects 220 the presence of slow-wave sleep, which is characterized by high activity in the delta frequency range (0.5 to 4 Hz) and by high density of sleep slow-waves (or delta waves). If slow-wave sleep is detected for a sufficiently long period of time and with a sufficient density of slow waves (e.g., number of slow waves per unit time), then the system applies the stimulation 222. The volume of the auditory stimulation is adjusted 224 between personalized and subjectively set minimum and maximum levels according to a volume titration algorithm. According to this algorithm, the volume remains unchanged if the EEG power in the delta frequency (also known as slow wave activity (SWA)) does not decrease over time (e.g., 15-second long blocks are used for this purpose), and increases by a fixed predefined rate per unit of time (e.g., 10% in 15 seconds) if the SWA decreases over time. The volume increase by the system attempts to counter the decreasing trend in the delta power.

The fact that the volume increases when SWA tends to decrease can often lead to a situation where the most intense stimulation occurs when sleep is naturally lightening. It is well known that sleep depth has a cyclic nature and that a hypnogram is only a practical but discrete approximation of an analogic process. If the maximum volume of tones, for example, (subjectively adjusted as described above) is underestimated, then the stimulation will disturb sleep and therefore defeat the purpose of the system. Such underestimation can easily happen especially if the environmental conditions where the volume is subjectively calibrated substantially differ (e.g. due to background noise) from that in the user's sleeping environment. Another disadvantage of the time based volume increase strategy (described above) is that the volume, for example, may be increased too slowly which can make the volume too low even if sleep is deep. These disadvantages are illustrated in FIG. 3.

Figure 3:
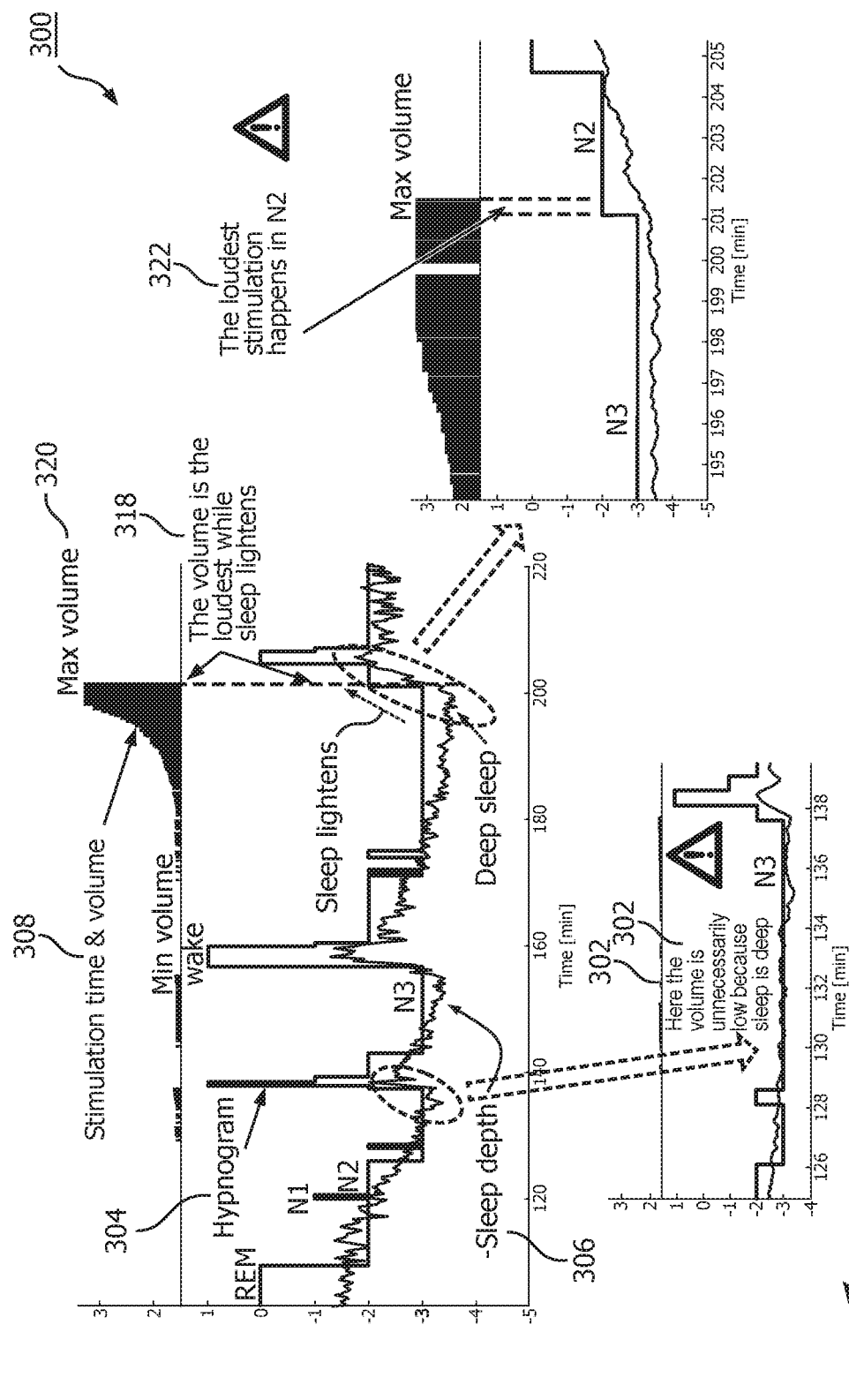
FIG. 3 illustrates intense stimulation during light sleep and an undesirable slow increase in stimulation intensity controlled by the EEG-based system.

FIG. 3 illustrates intense (e.g., loud) stimulation during light sleep 300 and an undesirably slow increase in stimulation intensity 302. FIG. 3 illustrates a manually scored hypnogram 304, an estimate of sleep depth 306 (e.g., displayed as a negative to show its correlation with hypnogram 304 so that the lower the line drops, the deeper the sleep is), and sensory stimulation 308. Because the volume increases when SWA tends to decrease, the loudest stimulation 320 can occur when sleep is naturally lightening 318. In this figure, loudest stimulation 320 is happening 322 in N2 which can disrupt sleep. In addition, around 130 minutes (as shown in lower portion 350 of FIG. 3), the volume of the stimulation is low even if sleep is deep.

Returning to FIG. 1, system 10 is configured to adjust stimulation intensity based on a real-time automated estimation of sleep depth. System 10 is configured to apply the loudest stimulation when sleep is the deepest. The estimation of sleep depth by system 10 is based on EEG features determined in real-time or near real-time. These features include power in the delta, alpha, and/or beta frequency bands, slow-wave amplitude and/or density, and/or other features.

Figure 4:
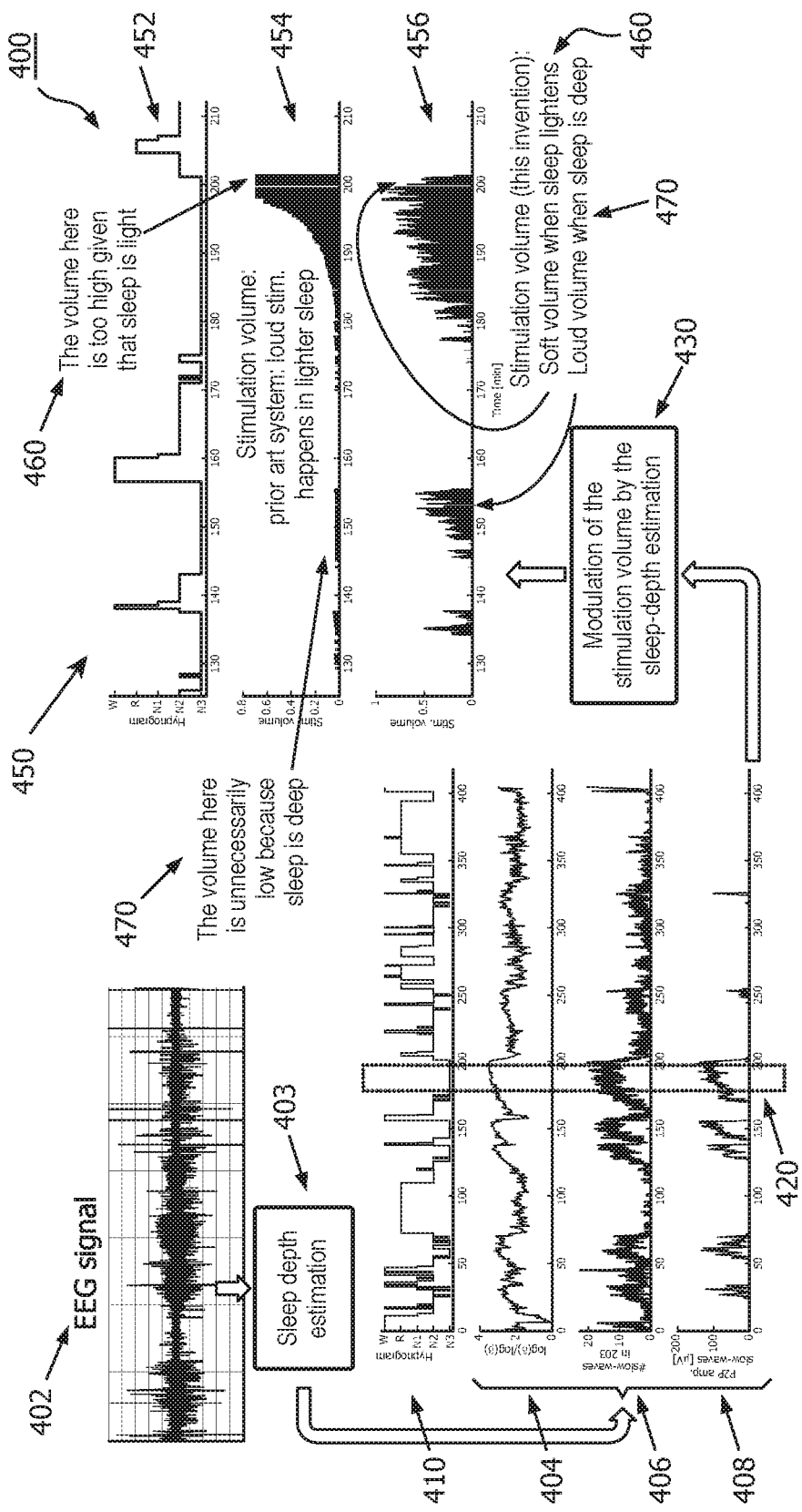
FIG. 4 summarizes the basic operations of the present system.

FIG. 4 summarizes the basic operations 400 of system 10 (FIG. 1). System 10 overcomes at least the deficiencies described above related to adjustment of stimulation intensity (e.g., volume). In system 10, intensity (e.g., volume) of stimulation delivered to subject 12 (FIG. 1) depends on sleep depth and/or other parameters. System 10 is configured such that the most intense (e.g., loudest) stimulation occurs when sleep is the deepest in subject 12. As shown in FIG. 4, system 10 is configured to estimate and/or otherwise determine 403 sleep depth in real-time or near real-time based on the EEG signal 402. System 10 is configured to determine sleep depth using one or more sleep depth determination methods. For example, three different determinations 404, 406, 408 of sleep depth using three different methods are shown in FIG. 4. A hypnogram 410 is shown for reference.

Sleep depth determination 404 includes taking the log of the ratio between the power in the delta band and the power in the beta band (delta-beta ratio) of EEG signal 402. This ratio correlates with sleep depth because the power in the delta band increases as sleep deepens and that the power in the beta band decreases as sleep deepens. However the power in these bands (taken individually) can be also influenced by artifacts or noise. Taking their ratio cancels the adverse influence of artifacts. In some embodiments, this ratio is determined in real-time or near real-time based on a filtered EEG signal 402 in the delta and beta bands and the running average (e.g., to ensure the smooth variation of this ratio a 30-second long (this is not intended to be limiting) averaging is used) of the squared filtered signals.

Sleep depth determination 406 includes detecting the number of slow-waves (during detected N3 sleep in subject 12) in a 20-second long window (the window duration of 20 seconds is only used for ease of visualization and is not intended to be limiting). The density of slow-waves positively correlates with sleep depth. The detection of slow-waves in real-time or near real-time from EEG signal is achieved by detecting a negative going zero-crossing followed by a positive going zero-crossing where the amplitude of the negative peak is below a predetermined threshold (e.g., −40 microvolts and/or any other threshold that allows system 10 to function as described herein) and the time period between the zero crossings is longer than a second predetermined threshold (e.g., 200 milliseconds and/or any other threshold that allows system 10 to function as described herein).

Sleep depth determination 408 includes determining the average peak-to-peak amplitude of detected slow-waves during N3 sleep. This parameter is smoothed in a 30-second long window. The 30 second long window is an example and is not intended to be limiting. This window may have any length that allows system 10 to function as described herein. It should be noted that sleep depth determinations 406 and 408 are related to the detection of slow waves during N3 sleep. However, sleep depth determination 404 may run independently of the detection of N3 sleep. In addition, as illustrated in FIG. 3, the three sleep depth determinations 404, 406, 408 are strongly positively correlated 420 and that they all reach their highest values during N3 sleep.

System 10 (FIG. 1) is configured to modulate 430 the stimulation intensity (e.g., volume) based on one or more of the sleep depth determinations 404, 406, 408, individually, and/or based on some combination of two or more of them. For example, system 10 may be configured such that a combination of two or more of the sleep depth determinations includes a weighted (e.g., using positive coefficients) addition and/or product of the sleep depth determinations, but other combinations are possible. An illustration 450 of the volume dynamics resulting from the sleep depth based modulation is shown in the upper right portion of FIG. 4. Illustration 450 includes a hypnogram 452 and corresponding stimulation intensities (volume) 454, 456. Stimulation intensity 454 is controlled by a prior art system (included for comparison with the present system) and stimulation intensity 456 is controlled by system 10. Illustration 450 shows at least two advantages (there are others, for example the rate of volume increase) of system 10 with respect to prior art systems. First, illustration 450 shows 460 how system 10 is configured such that the intensity (volume) is lower (softer) when sleep is lighter, which reduces the likelihood of disturbing sleep. Second, illustration 450 shows 470 how system 10 is configured such that the stimulation intensity (volume) is high (loud) when sleep is deep, which prevents situations in which the volume is unnecessarily low.

Returning to FIG. 1, in some embodiments, system 10 comprises one or more of a sensory stimulator 16, a sensor 18, a processor 20, electronic storage 22, a user interface 24, and/or other components. In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, some and/or all of the components of system 10 may be grouped as part of a headband and/or other garments worn by subject 12.

Sensory stimulator 16 is configured to provide sensory stimuli to subject 12. Sensory stimulator 16 is configured to provide sensory stimulation to subject 12 prior to a sleep session, during a current sleep session, after a sleep session, and/or at other times. For example, sensory stimulator 16 may be configured to provide sensory stimuli to subject 12 during slow wave sleep in a sleep session. Sensory stimulator 16 may be configured to provide sensory stimulation to subject 12 during a sleep session to induce, maintain, and/or adjust slow wave activity (indicated by EEG power in the 0.5 to 4 Hz band as described below) in subject 12. In some embodiments, sensory stimulator 16 may be configured such that adjusting includes increasing, decreasing, and/or other adjustment of slow wave activity (SWA) in subject 12. In some embodiments, the delivery of the sensory stimulation is timed to correspond to sleep stages associated with SWA, is timed to wake subject 12 from sleep, and/or timed to correspond to other sleep in subject 12.

In some embodiments, sensory stimulator 16 may be configured to induce and/or adjust SWA through non-invasive brain stimulation and/or other methods. Sensory stimulator 16 may be configured to induce and/or adjust SWA through non-invasive brain stimulation using sensory stimuli. The sensory stimuli include odors, sounds, visual stimulation, touches, tastes, and/or other stimuli. For example, transcranial magnetic stimulation may be applied to subject 12 to trigger, increase, and/or decrease SWA. As another example, sensory stimulator 16 may be configured to induce and/or adjust SWA via auditory stimulation of subject 12. Examples of sensory stimulator 16 may include one or more of a music player, a tone generator, a collection of electrodes on the scalp of subject 12, a unit to deliver vibratory stimulation (also known as somato-sensory stimulation), a coil generating a magnetic field to directly stimulate the brain's cortex, light generators, a fragrance dispenser, and/or other devices.

Sensor 18 is configured to generate output signals conveying information related to brain activity of subject 12 and/or other information. Sensor 18 is configured to generate output signals in an ongoing manner during the sleep session of subject 12, at regular intervals during the sleep session, and/or at other times. The brain activity of subject 12 may correspond to sleep depth, a current sleep stage, SWA in subject 12, and/or other characteristics of subject 12. The brain activity of subject 12 may be associated with rapid eye movement (REM) sleep, non-rapid eye movement (NREM) sleep, and/or other sleep. Sleep stages of subject 12 may include one or more of NREM stage N1, stage N2, or stage N3 sleep, REM sleep, and/or other sleep stages. In some embodiments, N1 corresponds to a light sleep state and N3 corresponds to a deep sleep state. In some embodiments, NREM stage 3 or stage 2 sleep may be slow wave (e.g., deep) sleep.

Sensor 18 may comprise one or more sensors that measure such parameters directly. For example, sensor 18 may be and/or include electrodes configured to detect electrical activity along the scalp of subject 12 resulting from current flows within the brain of subject 12. In some embodiments, one or more sensors 18 are EEG electrodes, and/or other sensors. An EEG exhibits changes throughout a sleep session. A prominent change in the EEG delta power (SWA) is typically visible, for example. SWA corresponds to the power of an EEG signal in the 0.5-4.5 Hz band. In some embodiments, this band is set to 0.5-4 Hz. SWA has a typical behavior throughout cyclic variations of a given sleep session. SWA increases during non-rapid eye movement sleep (NREM), declines before the onset of rapid-eye-movement (REM) sleep, and remains low during REM. SWA in successive NREM episodes progressively decreases from one episode to the next. SWA may be estimated, and/or slow wave sleep (e.g., stage N3) may be determined from an EEG for subject 12 during a given sleep session.

Sensor 18 may comprise one or more sensors that generate output signals conveying information related to brain activity of subject 12 indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12.

Although sensor 18 is illustrated at a single location near subject 12, this is not intended to be limiting. Sensor 18 may include sensors disposed in a plurality of locations, such as for example, coupled in a removable manner with the skin of subject 12, coupled in a removable manner with clothing of subject 12, worn by subject 12 (e.g., as a headband, wristband, etc.), within (or in communication with) sensory stimulator 16, positioned to point at subject 12 while subject 12 sleeps (e.g., a camera that conveys output signals related to movement of subject 12), and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, sensor 18), or processor 20 may represent processing functionality of a plurality of devices operating in coordination.

As shown in FIG. 1, processor 20 is configured to execute one or more computer program components. The one or more computer program components may comprise one or more of a parameter component 30, a sleep depth component 32, a control component 34, and/or other components. Processor 20 may be configured to execute components 30, 32, 34, and/or other components by software; hardware; firmware; some combination of software, hardware, and/or firmware; and/or other mechanisms for configuring processing capabilities on processor 20.

It should be appreciated that although components 30, 32, and 34 are illustrated in FIG. 1 as being co-located within a single processing unit, in embodiments in which processor 20 comprises multiple processing units, one or more of components 30, 32, 34, and/or other components may be located remotely from the other components. The description of the functionality provided by the different components 30, 32, 34, and/or other components described below is for illustrative purposes, and is not intended to be limiting, as any of components 30, 32, and/or 34 may provide more or less functionality than is described. For example, one or more of components 30, 32, and/or 34 may be eliminated, and some or all of its functionality may be provided by other components 30, 32, and/or 34. As another example, processor 20 may be configured to execute one or more additional components that may perform some or all of the functionality attributed below to one of components 30, 32, and/or 34.

Parameter component 30 is configured to determine brain activity parameters in subject 12 during the sleep session. Parameter component 30 is configured to determine the brain activity parameters based on the output signals and/or other information. In some embodiments, the one or more brain activity parameters include EEG related parameters such as power in various frequency bands of the EEG, ratios of power in a low frequency band to power in a high frequency band, and/or other parameters. In some embodiments, parameter component 30 is configured such that the one or more brain activity parameters are and/or are related to a frequency, amplitude, phase, and/or presence of specific sleep patterns such as spindles, K-complexes, or sleep slow waves, alpha waves, and/or other characteristics of the EEG signal. In some embodiments, determining the one or more brain activity parameters includes additively combining and/or performing other mathematical operations on the individual oscillatory components related to brain activity. For example, in some embodiments, the one or more brain activity parameters are determined based on the frequency, amplitude, and/or other characteristics of the EEG signal. In some embodiments, the determined brain activity parameters and/or the characteristics of the EEG may be and/or indicate sleep states that correspond to REM and/or NREM sleep stages. In some embodiments, the determined brain activity parameters are the REM and/or NREM sleep stages described above.

In some embodiments, the brain activity parameters include one or more of a power in a slow frequency band (e.g., about 0 to about 6 Hz) of an EEG signal, a power in a high frequency (e.g., about 8 to about 40 Hz), a ratio of power in a slow frequency band of an EEG signal to power in a high frequency band, the log of such a ratio, a density of slow waves in the subject, a peak to peak amplitude of the slow waves in subject 12, and/or other parameters. Parameter component 30 is configured to detect individual slow waves by detecting a negative going zero-crossing followed by a positive going zero-crossing in an EEG signal where the amplitude of the negative peak is below a predetermined threshold (e.g., −40 microvolts and/or any other threshold that allows system 10 to function as described herein) and the time period between the zero crossings is longer than a second predetermined threshold (e.g., 200 milliseconds and/or any other threshold that allows system 10 to function as described herein). In some embodiments, parameter component 30 is configured to determine brain activity parameters in subject 12 in an ongoing manner during the sleep session, at predetermined intervals during the sleep session, and/or at other times.

Sleep depth component 32 is configured to determine sleep depth in subject 12 during the sleep session. Sleep depth component 32 is configured to determine sleep depth based on one or more of the ratio of power in a slow frequency band of the EEG signal to the power in a high frequency band of the EEG signal, the density of slow waves, the peak to peak slow wave amplitude, and/or other information determined by parameter component 30, the information in the output signals from sensors 18, and/or other information. In some embodiments, sleep depth component 32 is configured to determine sleep depth based on a ratio (e.g., the delta-beta ratio and/or any other low slow frequency band power to high frequency band power ratio) determined in real-time or near real-time based on a filtered EEG signal (e.g., from sensor 18). In some embodiments, sleep depth component 32 determines a running average (e.g., to ensure the smooth variation of this ratio a 30-second long (this is not intended to be limiting) averaging is used) of squared filtered signals and determines the ratio based on this running average. In some embodiments, sleep depth component 32 is configured such that the sleep depth is the determined value of the ratio.

In some embodiments, sleep depth component 32 is configured to determine sleep depth based on a density of slow waves in subject 12. Sleep depth component 32 and parameter component 30 are configured such that density of slow waves in subject 12 is the number of slow-waves detected (e.g., by parameter component 30) during N3 sleep in subject 12 during time windows of predetermined lengths (e.g., a 20-second long window and/or a window of any other length that allows system 10 to function as described herein). The time windows of predetermined length may be set at manufacture, determined by sleep depth component 32 based on previous sleep of subject 12, set by a user via user interface 24, and/or determined by other methods. In some embodiments, sleep depth component 32 is configured such that the sleep depth is indicated by the number of slow waves in the predetermined time period.

In some embodiments, sleep depth component 32 is configured to determine sleep depth based on an average peak-to-peak amplitude of detected slow-waves during N3 sleep. Sleep depth component 32 may be configured such that this parameter is smoothed over a 30-second long window. The 30 second long window is an example and is not intended to be limiting. This window may have any length that allows system 10 to function as described herein. In some embodiments, sleep depth component 32 is configured such that the sleep depth is indicated by the average peak-to-peak amplitude of slow waves in subject 12.

In some embodiments, as described above, sleep depth component 32 is configured to determine sleep depth based on the power ratio, the slow wave density, and/or the slow wave amplitude alone. In some embodiments, sleep depth component 32 is configured to determine sleep depth by combining two or more of the power ratio, the slow wave density, and/or the slow wave amplitude. For example, in some embodiments, sleep depth component 32 is configured to combine two or more of the sleep depth determinations via a weighted (e.g., using positive coefficients) addition and/or product of the sleep depth determinations, but other combinations are possible. Sleep depth component 32 is configured such that any positive combination of these factors may be used to determine sleep-depth according to the equation:

$$d = k_1 \cdot g_1(\text{delta beta ratio}) + k_2 \cdot g_2(\text{slow-wave density}) + k_3 \cdot g_3(\text{slow-wave amplitude}),$$

where d is sleep depth, $k_1$, $k_2$, and $k_3$ are positive real constants and $g_1$, $g_2$, and $g_3$ are monotonically non-decreasing functions (for instance log functions).

Control component 34 is configured to control sensory stimulator 16 to provide sensory stimulation to subject 12. Control component 34 is configured to control sensory stimulator 16 to adjust the intensity of sensory stimulation provided to subject 12. Control component 34 is configured to control sensory stimulator 16 to adjust the intensity during the sleep session based on the determined sleep depth, and/or other information.

In some embodiments, control component 34 is configured to cause sensory stimulator 16 to incrementally increase or decrease an intensity (e.g., volume) of sensory stimulation (e.g., audible tones) delivered to subject 12 between a minimum threshold intensity (volume) and a maximum threshold intensity (volume) based on the determined sleep depth. In some embodiments, control component 34 is configured such that the minimum threshold intensity (volume) and the maximum threshold (volume) remain unchanged during the sleep session and are determined based on information related to brain activity in subject 12 from previous sleep sessions and/or based on other information (e.g., maximum and/or minimum frequencies and/or volumes subject 12 is able to perceive while awake). In some embodiments, control component 34 is configured such that the volume limits are subjectively set by, for instance, setting the minimum volume to the hearing threshold of subject 12 and the maximum volume to the volume level that can wake up subject 12 (e.g., the volume of a wake up alarm set by subject 12). It is also possible that the volume limits are set by analyzing the sleep EEG data from a calibration night and identifying sensitive subjects. Alternatively the volume limits can be set based demographic factors and/or other information.

Figure 5:
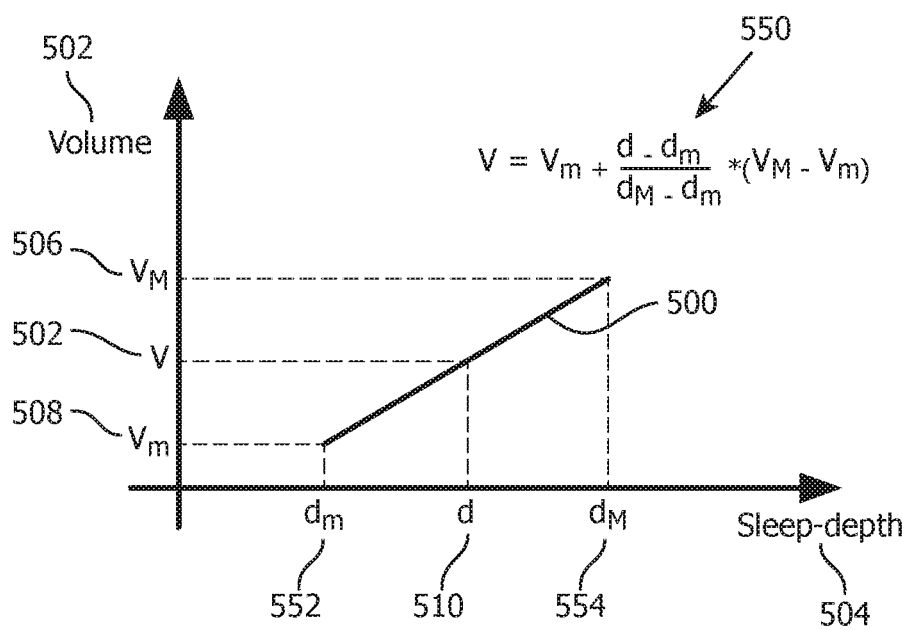
FIG. 5 illustrates adjustment of stimulation volume of auditory tones based on sleep depth between a maximum threshold volume and a minimum threshold volume.

By way of a non-limiting example, FIG. 5 illustrates adjustment 500 of stimulation volume 502 of auditory tones based on sleep depth 504 between a maximum threshold volume 506 and a minimum threshold volume 508. In FIG. 5, the sleep depth is illustrated as "d" 510, and in this example, is estimated as the sum of the delta-beta ratio, the slow-wave density, and the slow-wave amplitude. The minimum and maximum volume ($V_m$ 508 and $V_M$ 506 respectively) remain unchanged during the sleep session and were determined based on information related to brain activity in subject 12 (FIG. 1) from previous sleep sessions and/or at other times. In FIG. 5, adjustment 500 of the volume of the sensory stimulation based on the sleep depth follows a first order equation 550. In this model, $d_m$ 552 and $d_M$ 554 are the limits of sleep depth within which the volume of the stimulation is to be modulated. First order equation 550 relating volume and sleep depth should not be considered limiting. Other functions are possible.

Returning to FIG. 1, in some embodiments, control component 34 is configured to modulate the rate of volume change. From auditory perceptual research it is known that humans are more sensitive to volume changes as compared to the absolute volume level. In this embodiment, control component 34 proportionally modulates the rate of volume change based on the sleep depth as shown in the equation below.

$$V_{t-1}$$

where d is the sleep-depth, $V_t$ and $V_{t-1}$ are the volumes at time t and t−1 respectively, and k is a positive constant. According to this equation, the rate of change in volume is proportional to sleep depth.

In some embodiments, as described above, control component 34 is configured to determine the minimum threshold intensity (volume) and the maximum threshold (volume) remain based on information related to brain activity in subject 12 from previous sleep sessions and/or based on other information (e.g., maximum and/or minimum frequencies and/or volumes subject 12 is able to perceive while awake). For example, the maximum and/or minimum threshold intensities may be determined based on information gathered during one or more calibration nights of sleep for subject 12. In some embodiments, the maximum and/or minimum threshold intensities may be determined based on information from a population of several subjects. For example, given the knowledge of the volume limits for a population of demographically matching users, the minimum (and/or maximum) volume limit for a target user (e.g., subject 12) can be set to the average across the demographically matching population of the volume minima (and/or maxima).

In some embodiments, control component 34 is configured to adjust the minimum threshold intensity (e.g., volume) and the maximum threshold intensity during the sleep session based on previous sleep depth estimates during the sleep session. Updating these parameters dynamically takes into account sleep-cycle sleep-depth variability. In some embodiments, control component 34 is configured to update the minimum ($d_m$) and maximum ($d_M$) sleep depth threshold levels based on the following equations:

$$d_m \leftarrow \mu \cdot d_m(\text{history}) + (1-\mu) d_m(\text{current sleep episode}),$$
and $$d_M \leftarrow \mu \cdot d_M(\text{history}) + (1-\mu) d_M(\text{current sleep episode});$$

where the "history" term refers to the values used in a previous sleep episode (default values if the current sleep episode is the first one) and the term "current sleep episode" corresponds to the sleep-depth estimates from the previous sleep-cycle in the current sleep episode. The update parameter $\mu$ is in the interval between 0 and 1 (e.g., 0.2) and controls the weight of the current sleep episode estimate with respect to the previous history.

In some embodiments, control component 34 is configured such that controlling sensory stimulator 16 to adjust the intensity of sensory stimulation provided to subject 12 during the sleep session comprises determining a rate of change in the sleep depth during the sleep session. In such embodiments, control component 34 may be configured to control sensory stimulator 16 to adjust the intensity of sensory stimulation provided to subject 12 during the sleep session based on the determined rate of change in the sleep depth. In this embodiment, the volume level is adjusted proportionally to the change in sleep depth as shown in the equation below.

$$V = k \frac{d_t - d_{t-1}}{d_{t-1}},$$

where V is the volume level, k is a positive constant, and $d_t$ and $d_{t-1}$ are the sleep-depth determinations at time t and t−1 respectively. In such embodiments, control component 34 may be configured to control sensory stimulator 16 to adjust the intensity of sensory stimulation provided to subject 12 during the sleep session based on one or the other of the determined sleep depth or the rate of change in the sleep depth, and/or control component 34 may be configured to control sensory stimulator 16 based on some combination of the determined sleep depth and the determined rate of change in the sleep depth.

Figure 6:
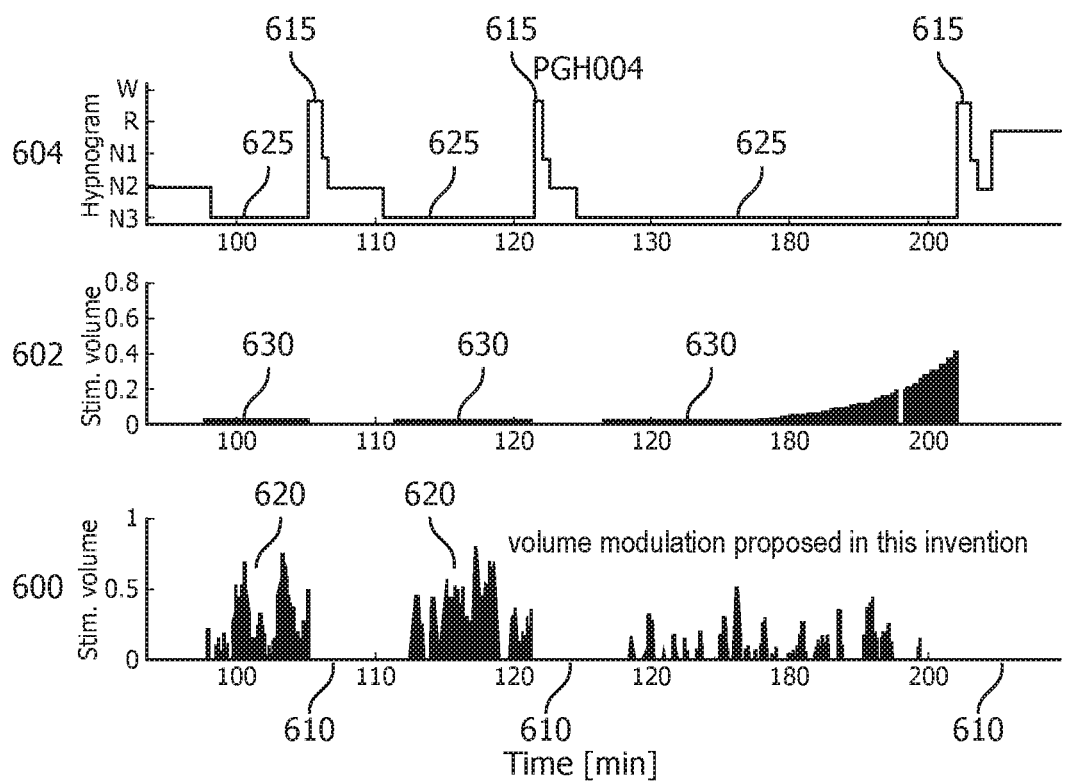
FIG. 6 illustrates operation of the present system relative to operation of a prior art system for an individual subject

FIG. 6 illustrates operation 600 of system 10 (FIG. 1) relative to operation 602 of a prior art system for an individual subject (PGHOO4). A manually scored hypnogram 604 is also shown for reference. With system 10, delivering intense (e.g., loud) stimulation when sleep is lightening 615 is prevented 610. In addition, system 10 avoids providing stimulation with an unnecessarily low intensity (e.g., volume) 620 during deep sleep 625, unlike the prior art system where the intensity (volume) is unnecessarily low 630.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 7:
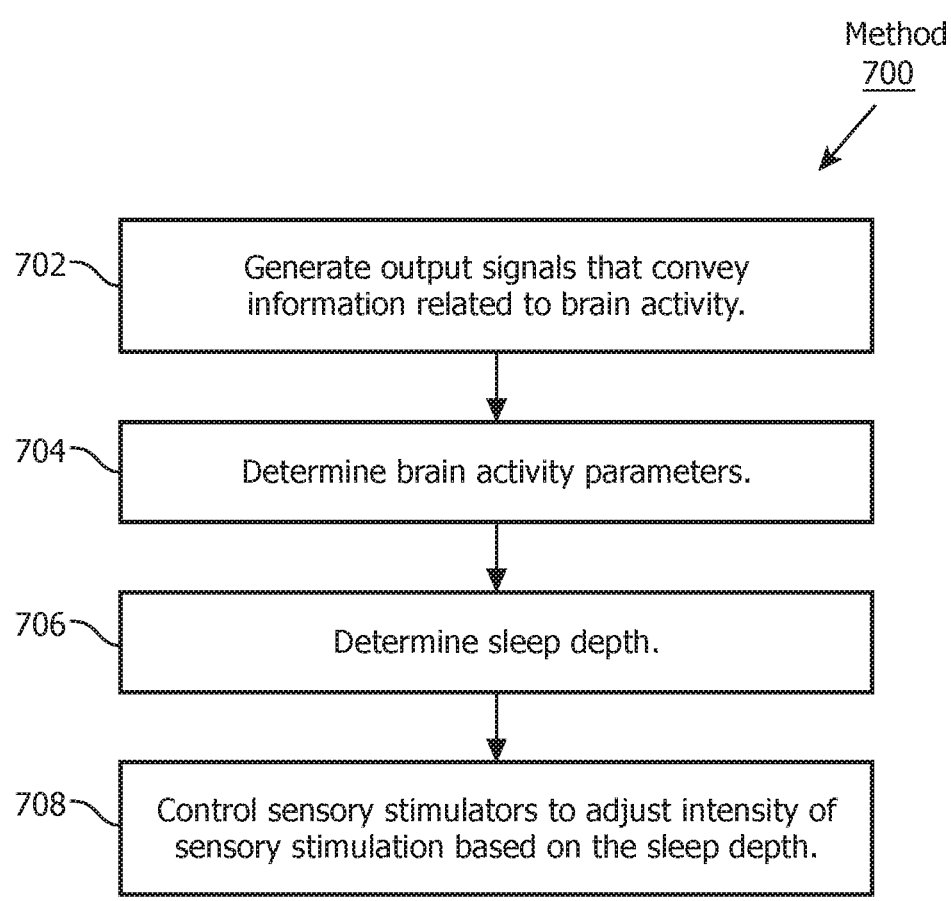
FIG. 7 illustrates a method for adjusting an intensity of sensory stimulation delivered to a subject during a sleep session with an adjustment system.

FIG. 7 illustrates a method 700 for adjusting an intensity of sensory stimulation delivered to a subject during a sleep session with an adjustment system. The system comprises one or more sensory stimulators, one or more sensors, one or more hardware processors, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, output signals conveying information related to brain activity of the subject during a sleep session are generated. In some embodiments, operation 702 is performed by one or more sensors the same as or similar to sensors 18 (shown in FIG. 1 and described herein).

At an operation 704, brain activity parameters are determined. The brain activity parameters are determined based on the output signals and/or other information. The brain activity parameters include a ratio of power in a slow frequency band of an electroencephalogram (EEG) signal to power in a high frequency band, a density of slow waves in the subject, a peak to peak amplitude of the slow waves in the subject, and/or other parameters. In some embodiments, operation 704 is performed by a hardware processor component the same as or similar to parameter component 30 (shown in FIG. 1 and described herein).

At an operation 706, sleep depth is determined. The sleep depth is determined based on one or more of the ratio, the density of slow waves, the peak to peak slow wave amplitude, and/or other information. In some embodiments, determining sleep depth in the subject during the sleep session comprises determining a rate of change in the sleep depth during the sleep session. In some embodiments, operation 706 is performed by a hardware processor component the same as or similar to sleep depth component 32 (shown in FIG. 1 and described herein).

At an operation 708, the sensory stimulators are controlled to adjust intensity of sensory stimulation provided to the subject based on the determined sleep depth. In some embodiments, the sensory stimulation comprises audible tones, and operation 708 includes incrementally increasing or decreasing a volume of the audible tones between a minimum threshold volume and a maximum threshold volume based on the determined sleep depth. In some embodiments, the minimum threshold volume and the maximum threshold volume remain unchanged during the sleep session and are determined based on information related to brain activity in the subject from previous sleep sessions. In some embodiments, operation 708 includes adjusting the minimum threshold volume and the maximum threshold volume during the sleep session based on previous sleep depth estimates during the sleep session. In some embodiments, the intensity of sensory stimulation provided to the subject during the sleep session is adjusted based on the determined rate of change in the sleep depth. In some embodiments, operation 708 is performed by a hardware processor component the same as or similar to control component 34 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to adjust an intensity of sensory stimulation delivered to a subject during a sleep session, the system comprising:

one or more sensory stimulators configured to provide sensory stimulation to the subject;

one or more sensors configured to generate output signals conveying information related to brain activity in the subject during the sleep session; and one or more hardware processors operatively communicating with the one or more sensory stimulators and the one or more sensors, the one or more hardware processors configured by machine-readable instructions to:

determine brain activity parameters in the subject during the sleep session based on the output signals, the brain activity parameters including one or more of a density of slow waves in the subject and a peak to peak amplitude of the slow waves in the subject;

determine sleep depth in the subject during the sleep session based on one or more of the density of slow waves and the peak to peak slow wave amplitude; and control the one or more sensory stimulators to adjust the intensity of sensory stimulation provided to the subject during the sleep session based on the determined sleep depth.

2. The system of claim 1, wherein the one or more sensory stimulators are configured such that the sensory stimulation comprises audible tones, and wherein the one or more hardware processors are configured to cause the one or more sensory stimulators to incrementally increase or decrease a volume of the audible tones between a minimum threshold volume and a maximum threshold volume based on the determined sleep depth.

3. The system of claim 2, wherein the one or more hardware processors are configured such that the minimum threshold volume and the maximum threshold volume remain unchanged during the sleep session and are determined based on information related to brain activity in the subject from previous sleep sessions.

4. The system of claim 2, wherein the one or more hardware processors are configured to adjust the minimum threshold volume and the maximum threshold volume during the sleep session based on previous sleep depth estimates during the sleep session.

5. The system of claim 2, wherein the one or more hardware processors are configured to adjust the minimum threshold volume and the maximum threshold volume based on corresponding volume thresholds for a demographically similar population.

6. The system of claim 1, wherein the one or more hardware processors are configured such that the determined sleep depth is between a minimum sleep depth threshold and a maximum sleep depth threshold, the minimum sleep depth threshold and the maximum sleep depth threshold determined based on corresponding sleep depth thresholds for a demographically similar population.

7. The system of claim 1, wherein the one or more hardware processors are configured such that controlling the sensory stimulators to adjust the intensity of sensory stimulation comprises determining a rate of change in the sleep depth during the sleep session; and the one or more sensory stimulators are controlled to adjust the intensity of sensory stimulation provided to the subject during the sleep session based on the determined rate of change in the sleep depth.

8. A method for adjusting an intensity of sensory stimulation delivered to a subject during a sleep session with an adjustment system, the system comprising one or more sensory stimulators, one or more sensors, and one or more hardware processors, the method comprising:

generating, with the one or more sensors, output signals conveying information related to brain activity in the subject during the sleep session;

determining, with the one or more hardware processors, brain activity parameters in the subject during the sleep session based on the output signals, the brain activity parameters including one or more of a density of slow waves in the subject and a peak to peak amplitude of the slow waves in the subject;

determining sleep depth in the subject during the sleep session based on one or more of the density of slow waves and the peak to peak slow wave amplitude; and controlling the one or more sensory stimulators to adjust the intensity of sensory stimulation provided to the subject during the sleep session based on the determined sleep depth.

9. The method of claim 8, wherein the sensory stimulation comprises audible tones, and wherein the method further comprises incrementally increasing or decreasing a volume of the audible tones between a minimum threshold volume and a maximum threshold volume based on the determined sleep depth.

10. The method of claim 9, wherein the minimum threshold volume and the maximum threshold volume remain unchanged during the sleep session and are determined based on information related to brain activity in the subject from previous sleep sessions.

11. The method of claim 9, further comprising adjusting the minimum threshold volume and the maximum threshold volume during the sleep session based on previous sleep depth estimates during the sleep session.

12. The method of claim 9, further comprising adjusting the minimum threshold volume and the maximum threshold volume based on corresponding volume thresholds for a demographically similar population.

13. The method of claim 8, wherein the determined sleep depth is between a minimum sleep depth threshold and a maximum sleep depth threshold, the minimum sleep depth threshold and the maximum sleep depth threshold determined based on corresponding sleep depth thresholds for a demographically similar population.

14. The method of claim 8, wherein controlling the sensory stimulators to adjust the intensity of sensory stimulation comprises determining a rate of change in the sleep depth during the sleep session; and the intensity of sensory stimulation provided to the subject during the sleep session is adjusted based on the determined rate of change in the sleep depth.

15. A system for adjusting an intensity of sensory stimulation delivered to a subject during a sleep session, the system comprising:

means for providing sensory stimulation to the subject;

means for generating output signals conveying information related to brain activity in the subject during the sleep session;

means for determining brain activity parameters in the subject during the sleep session based on the output signals, the brain activity parameters including one or more of a density of slow waves in the subject and a peak to peak amplitude of the slow waves in the subject;

means for determining sleep depth in the subject during the sleep session based on one or more of the density of slow waves and the peak to peak slow wave amplitude; and means for controlling the means for providing sensory stimulation to adjust the intensity of sensory stimulation provided to the subject during the sleep session based on the determined sleep depth.

16. The system of claim 15, wherein the means for providing sensory stimulation are configured such that the sensory stimulation comprises audible tones, and wherein the means for controlling are configured to cause the means for providing sensory stimulation to incrementally increase or decrease a volume of the audible tones between a minimum threshold volume and a maximum threshold volume based on the determined sleep depth.

17. The system of claim 16, wherein the means for controlling are configured such that the minimum threshold volume and the maximum threshold volume remain unchanged during the sleep session and are determined based on information related to brain activity in the subject from previous sleep sessions.

18. The system of claim 16, wherein the means for controlling are configured to adjust the minimum threshold volume and the maximum threshold volume during the sleep session based on previous sleep depth estimates during the sleep session.

19. The system of claim 16, wherein the means for controlling are configured to adjust the minimum threshold volume and the maximum threshold volume based on corresponding volume thresholds for a demographically similar population.

20. The system of claim 15, wherein the means for determining sleep depth are configured such that the determined sleep depth is between a minimum sleep depth threshold and a maximum sleep depth threshold, the minimum sleep depth threshold and the maximum sleep depth threshold determined based on corresponding sleep depth thresholds for a demographically similar population.

21. The system of claim 15, wherein the means for controlling are configured such that controlling the means for providing sensory stimulation to adjust the intensity of sensory stimulation comprises determining a rate of change in the sleep depth during the sleep session; and the means for providing sensory stimulation are controlled to adjust the intensity of sensory stimulation provided to the subject during the sleep session based on the determined rate of change in the sleep depth.

* * * * *